United States Patent [19]  [11] 4,323,570
Stenzel et al. [45] Apr. 6, 1982

[54] SUBSTITUTED AMINOPYRIMIDINES

[75] Inventors: Wolfgang Stenzel; Wolfgang Fleck; Erich Cohnen; Ben Armah, all of Hamburg, Fed. Rep. of Germany

[73] Assignee: Beiersdorf Aktiengesellschaft, Fed. Rep. of Germany

[21] Appl. No.: 92,134

[22] Filed: Nov. 7, 1979

[30] Foreign Application Priority Data

Nov. 15, 1978 [DE] Fed. Rep. of Germany ....... 2849537
Sep. 13, 1979 [DE] Fed. Rep. of Germany ....... 2937023

[51] Int. Cl.$^3$ ............................................ C07D 239/20
[52] U.S. Cl. .................................... 424/251; 544/322; 544/320; 544/324; 544/316; 544/310
[58] Field of Search ............... 544/300, 310, 316, 333, 544/322, 320, 324; 424/251

[56] References Cited

U.S. PATENT DOCUMENTS 3,818,033 6/1974 Heyes et al. .................... 544/333
3,872,121 3/1975 Kummer et al. ................ 424/251
3,920,655 11/1975 Rufer et al. .................... 544/333
4,029,792 6/1977 Danielewicz .................... 424/251
4,108,982 8/1978 Amschler ....................... 424/272

FOREIGN PATENT DOCUMENTS 1267433 3/1972 United Kingdom .

OTHER PUBLICATIONS

Hackh's Chemical Dictionary, p. 16, fourth edition (1969), McGraw-Hill, NY.
Weygand–Hilgetag, Organisch Chemische Experimentierkunst, 4th Edition, Joh. Ambr. Barth, Leipzig (1970), 515–516.
B. Helwig, Modrine Arzneimittel, 4th edition (1972), 926–928.

Primary Examiner—Nicholas S. Rizzo
Attorney, Agent, or Firm—Bierman & Bierman

[57] ABSTRACT

The present invention is directed to certain aminopyrimidines of the general formula

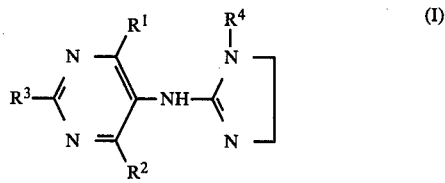

wherein $R^1$, $R^2$, and $R^3$ are hydrogen, halogen, alkoxy, alkylthio, or alkyl having 1 to 4 carbon atoms, or cycloalkyl having 3 to 5 carbon atoms and $R^4$ is hydrogen or an aliphatic or aromatic acyl group, as well as physiologically compatible acid addition salts thereof. Compounds of the present invention are useful as blood pressure lowering agents and in the treatment of glaucoma.

9 Claims, No Drawings

SUBSTITUTED AMINOPYRIMIDINES

This application claims the priorities of German Applications Nos. P 28 49 537.6 and P 29 37 023.8, filed Nov. 15, 1978 and Sept. 13, 1979, respectively.

The substances of the present invention are aminopyrimidines which have particularly desirable antihypertensive effects and are also suitable for the treatment of glaucoma. Such compounds are especially noted for their long-lasting effects.

The inventive compounds are substituted 5-(2-imidazolin-2-yl)-aminopyrimidines of the formula (I).

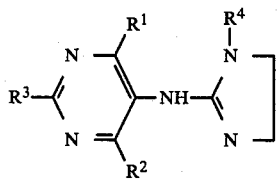

wherein $R^1$, $R^2$, and $R^3$ are hydrogen or halogen atoms, or alkoxy, alkylthio or alkyl groups, all of which have 1 to 4 carbon atoms. Alternatively, they can be a cycloalkyl group having 3 to 5 carbon atoms. $R^1$, $R^2$, and $R^3$ may be the same or different. $R^4$ is hydrogen or an aliphatic or aromatic acyl group. Also included within the scope of the present invention are the physiologically compatible acid addition salts of the foregoing compounds, in addition to methods for their production and use.

The preferred compounds are those which are substituted in the 4 or 6 position of the pyrimidine radical, especially those which are halogenated in either of those positions. The compounds can be used as such or in the form of their acid addition salts. As is customary, they may be mixed with the usual vehicles, diluents, etc. and prepared in the form of injectible solutions or as dragees, tablets, or liquids for oral administration. Typical carriers are lactose, gelatin, cornstarch, stearic acid, ethanol, propylene glycol, ethers of tetrahydrofurfuryl alcohol, and water.

The compounds produce a long-lasting blood pressure lowering in renal and spontaneously hypertensive rats when administered orally at a dosage level of 1 to 30 mg. The preferred dosage in humans is approximately 1 to 10 mg per day.

The compounds of the present invention may be prepared by reacting the corresponding 5-aminopyrimidines of the general formula II

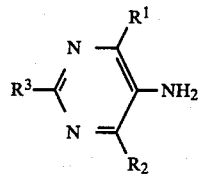

with 1-acyl-imidazolidin-2-ones of the general formula III

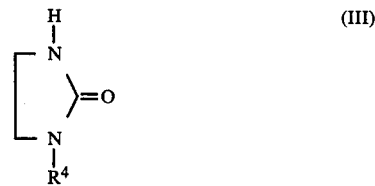

wherein $R^4$ is an aliphatic or aromatic acyl group. Typically, the group is formyl, acetyl, propionyl, or butyryl. In addition, these groups can have an aromatic substituent such as the phenyl group. Compounds of formulas II and III are well-known or obtainable in accordance with known methods of preparation.

The cycloalkyl substituents which are particularly suitable are cyclopropyl, cyclobutyl, cyclopentyl and alkyl derivatives thereof.

The aminopyrimidines substituted by alkyl or cycloalkyl groups in the 2 position can be obtained from the correspondingly substituted imino ethers. Starting with the nitriles, amidines are cyclized with malonic esters to form the hydroxypyrimidine derivatives. Then, the desired substituted halogenated aminopyrimidines are formed by halogenation with exchange of hydroxy groups and the introduction of the amino group over the nitrile group.

If aminopyrimidines substituted in the 2 and 4 position are desired, one begins by halogenation of the corresponding 6-uracils and introduction of the amino group as previously described.

The reaction between the aminopyrimidines and the acylimidazolidinones can be carried out in the presence of phosphorous oxidetrichloride between 20° C. and the boiling point of the phosphorous oxidetrichloride. The reaction takes between 3 and 70 hours. It is preferred that an excess of the phosphorous compound be used so that is also serves as a solvent. However, inert organic solvents may also be used. Most preferable, in the event that phosphorous oxidetrichloride is used alone, is a reaction time of approximately 50 hours at temperatures between 50° and 100° C. After removing the excess phosphorous oxidetrichloride with water or by means of an aqueous alkaline medium (e.g. sodium carbonate solution or lye), the reaction product is converted to the acyl derivatives, preferably at reduced temperature.

For the compounds in which $R^4$ is hydrogen, the acyl group can be split off by the use of mineral acids, organic acids, and/or alkaline reagents. Advantageously, acetic acid, lye, sodium carbonate, alkali alcoholates or amines may be used. It is especially preferred to remove the acetyl group by heating with water or aliphatic alcohols. Methanol is particularly useful for this purpose. This means of removal is particularly gentle and, for that reason, desirable.

It is also possible to convert the compounds wherein $R^4$ is hydrogen to the acyl form by reacting in a known manner with a recognized acylating agent. In this manner, new 1-acylimidazolines are obtained. Typical acylating agents are acid anhydrides and acid chlorides in the presence of bases such as pyridine. In this manner, such acyl groups as formyl, acetyl, propionyl, or butyryl groups may be introduced. These groups can also have an aromatic substituent, such as the phenyl group. The acetyl substituent has been found preferable.

Physiologically compatible acid addition salts of the foregoing compounds can be made in the usual manner.

Salts of, for example, mineral acids, such as hydrochloric acid, hydrobromic acid and sulfuric acid; or organic acids, such as malonic acid, maleic acid, fumaric acid, and oxalic acid are all suitable.

The corresponding alkoxy and alkylthio compounds can also be obtained from the halogenated compounds by substitution of the halogen atoms under suitable reaction conditions. The halogen substituents on the pyrimidine radical can be converted to alkoxy groups by the use of alcohols or alcoholates, preferably at a temperature between 0° C. and the boiling point of the alcohol or alcoholates. Depending upon the reaction conditions, one or more alkoxy groups can be substituted for a corresponding number of halogen atoms.

If desired, the reaction can be carried out so that, by a suitable selection of the conditions (temperature, reaction time, concentration of reactants, etc.) at least one halogen atom attached to the pyrimidine radical is still available. If this is done, the alkylthio compounds according to the invention can be prepared. Moreover, under more extreme conditions of higher temperature, longer reaction time, and higher alcohol or alcoholate concentration, additional halogen atoms can be converted. Also, separation of the $R^4$ acyl group is possible.

The reactions in question are carried out either at room temperature or higher temperatures, preferably with alcohols or diluted alcohol solutions. Suitable are alcohols (and alcoholates) having 1 to 4 carbon atoms, especially methanol and ethanol.

It is also possible to produce compounds of Formula I wherein $R^1$ is halogen, hydrogen, alkoxy, alkylthio, or alkyl with 1 to 4 carbon atoms or a cycloalkyl group with 3 to 5 carbon atoms; $R^2$ is alkoxy having 1 to 4 carbon atoms; $R^3$ is hydrogen, alkoxy, alkylthio, or alkyl having 1 to 4 carbon atoms, or a cycloalkyl group having 3 to 5 carbon atoms; and $R^4$ is hydrogen. To do so, the compounds of Formula I wherein $R^1$ is a halogen or hydrogen atom, or an alkylthio or alkyl group having 1 to 4 carbon atoms, or a cycloalkyl group with 3 to 5 carbon atoms; $R^2$ is halogen; $R^3$ is hydrogen, halogen, or an alkylthio or alkyl group with 1 to 4 carbon atoms, or a cycloalkyl group with 3 to 5 carbon atoms; and $R^4$ is acyl or hydrogen, are used as starting materials.

The introduction of alkoxy groups is also possible in accordance with the above-described method if there are alkylthio substituents present particularly in the case of those compounds wherein $R^1$ is halogen, $R^2$ is either alkylthio or cycloalkyl, and $R^3$ is hydrogen, alkyl with 1 to 4 carbon atoms, or cycloalkyl, the halogen substituent can be substituted by the corresponding alkoxy group having 1 to 4 carbon atoms in the presence of alcohols or alcoholates at temperatures of between 0° C. and the boiling point of the alcohol or alcoholate used.

Moreover, the conversion of halogen substituents on the pyrimidine radical to alkylthio groups is carried out in a manner analogous to that described for the substitution of alkoxy groups for the halogens. Alkylmercaptans are used and, it has been found, the preferred temperature range is from 20° C. to the boiling temperature of the solvent. The method is operable as low as 0° C. As in the case of the alkoxy introduction, leaving at least one halogen atom linked with the pyrimidine radical and available for synthesis of other compounds of this invention is useful. It permits an exchange in the presence of alkoxy substituents. The additional halogens can be reacted under more extreme conditions of temperature reaction time and alkali mercaptide concentration. The preferred material is a suspension of sodium methyl mercaptide in toluene.

In the foregoing manner, compounds having alkylthio substituents are preferably obtained from the compounds of Formula I wherein $R^1$ and $R^3$ are halogen, hydrogen, or alkyl or alkoxy with 1 to 4 carbon atoms or a cycloalkyl group having 3 to 5 carbon atoms; $R^2$ is halogen, and $R^4$ is hydrogen or an aliphatic or aromatic acyl group. The compounds can be obtained by substituting the halogen substituents with the desired radicals.

By a suitable selection of reaction conditions, some or all of $R^1$, $R^2$, and $R^3$ may be halogen atoms and such compounds can be used for further substitution by alkoxy or alkylthio groups in any desired order or combination.

The compounds of Formula I can also be prepared by reacting the S-alkylisothiouronium salts of Formula IV

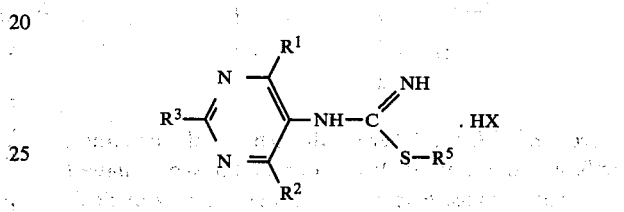

with ethylene diamine in a known manner. $R^5$ is alkyl, preferably methyl and X is halogen. One method for carrying out this reaction is by heating the two reactants for several hours in solvents, such as alcohol. Methanol is particularly preferred. In this reaction, the S-methylisothiouronium salts are preferred.

The starting compounds for the preparation of the compounds of Formula IV can be obtained by known methods from the corresponding 5-aminopyrimidine derivatives of Formula II

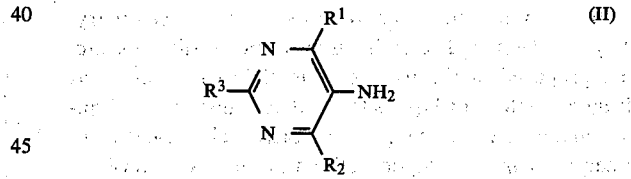

It is only necessary to start from those compounds wherein $R^1$, $R^2$, and $R^3$ represent the appropriate desired substituents.

The compounds of Formula II can be reacted with benzoylisothiocyanate to form the corresponding benzoyl thioureas. These can be hydrolized to the pyrimidyl thioureas of Formula V

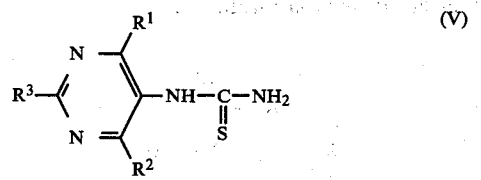

The benzoylisothiocyanate is obtained by the reaction between ammonium thiocyanate and benzoylchloride. The compounds of Formula V can then be reacted with methyliodide or other simiilar methylating agents to form the S-methylisothiouronium salts of Formula IV.

The pyrimidyl benzoylthioureas are preferably prepared by the reaction of ammonium thiocyanate, benzoylchloride and aminopyrimidine in a heated solvent, preferably boiling acetone. The thiourea derivatives obtained are then hydrolized in order to separate the benzoyl radical. The hydrolization can take place, for example, in the presence of bases and, if necessary, with heating. Lye is particularly suitable for this purpose. The substituted thioureas are suspended, for example in acetone, and converted by methylating agents (preferably methyl iodide) to isothiouroniumiodide. The reaction is preferably carried out in boiling acetone.

The following examples are intended to illustrate the present invention.

EXAMPLE 1

4,6-dichloro-2-methyl-5-(1-acetyl-2-imidazolin-2-yl)-aminopyrimidine 20 g 5-amino-4,6-dichloro-2-methylpyrimidine, 15 g 1-acetyl-2-imidazolidin-2-one and 200 ml phosphorous oxide trichloride are stirred for 48 hours at 50° C. phosphorous oxide trichloride is distilled off in the vacuum. The residue is then put into ice water and neutralized with potassium carbonate. After extraction with chloroform, the chloroform solution is evaporated and the residue crystallized from 700 ml methanol/acetic ester (1:1), and 16.5 g of 4,6-dichloro-2-methyl-5-(1-acetyl-2-imidazolin-2-yl) aminopyrimidine is obtained. Melting point 257° C.

EXAMPLE 2

4-chloro-2-methyl-6-methylthio-5-(2-imidazolin-2-yl)-aminopyrimidine 8 g 4,6-dichloro-2-methyl-5-(1-acetyl-2-imidazolin-2-yl)-amino-pyrimidine in 25 ml absolute toluene are mixed with a suspension of 3 g sodium methyl mercaptide in 25 ml toluene and stirred for 3 hours at 40° C. After cooling, the solid substance is vacuum dried, placed in 300 ml water, and extracted twice with 250 ml chloroform each. The organic phase is dried and evaporated. The residue is recrystallized from methanol. Yield: 5.79 g of 4-chloro-2-methyl-6-methylthio-5-(2-imidazolin-2-yl)-aminopyrimidine crystals. Melting point: 233° C. (decomposition).

For the preparation of the hydrochloride, 5.5 g of the base in 15 ml of a solution of hydrochloric acid in ethanol (10) is mixed with 45 ml of ether and cooled. The hydrochloride of 4 chloro-2-methyl-6-methylthio-5-(2-imidazolin-2-yl)-aminopyrimidine is obtained. Melting point: 214° C. (decomposition).

EXAMPLE 3

4-chloro-6-methoxy-2-methyl-5-(2-imidazolin-2-yl)-aminopyrimidine 10 g 4,6-dichloro-2-methyl-5-(1-acetyl-2-imidazolin-2-yl)-aminopyrimidine are mixed with a solution of 3.78 g sodium methylate in 35 ml methanol and boiled for 2 hours. Then 100 ml water are added, cooled, and vacuum dried. 7.2 g of 4-chloro-6-methoxy-2-methyl-5-(2-imidazolin-2-yl)-aminopyrimidine is obtained. (Melting point 217°–219° C., decomposition) from nitromethane.

For the preparation of the hydrochloride, the base is suspended in 20 ml water and brought with hydrochloric acid to a pH of 3. The solution is evaporated, the residue washed with some ethanol and ether and vacuum dried. 6.9 g 4-chloro-6-methoxy-2-methyl-5-(2-imidazolin-2-yl)-aminopyrimidine as the hydrochloride is obtained. Melting point: 189° C. (decomp.)

EXAMPLE 4

4,6-di-methylthio-2-methyl-5-(2-imidazolin-2-yl)-aminopyrimidine 5 g 4,6-dichloro-2-methyl-5-(1-acetyl-2-imidazolin-2-yl)-aminopyrimidine are dissolved in 20 ml toluene and mixed with a suspension of 2.4 g sodium methyl mercaptide in 20 ml toluene and heated for 15 hours under reflux. After cooling, the solid substance is vacuum dried, placed in 200 ml water, and extracted twice with 200 ml chloroform each time. The combined organic phase is evaporated and the residue is purified on silica gel by column chromatography. (developer: chloroform/methanol 40:5). 3.1 g of 4,6-di-methylthio-2-methyl-5-(2-imidazolin-2-yl)-aminopyrimidine is obtained. Melting point 260° C. (decomp.).

EXAMPLE 5

4-methoxy-2-methyl-6-methylthio-5-(2-imidazolin-2-yl)-aminopyrimidine 3 g 4-chloro-2-methyl-6-methylthio-5-(2-imidazolin-2-yl)-aminopyrimidine (Example 2) are mixed with 60 ml 15% methanolic sodium methylate solution and boiled for 4 hours under reflux. Then about 40 ml methanol are distilled off. The solution is mixed with water and cooled until it crystallizes. 1.5 g of 4-methoxy-2-methyl-6-methylthio-5-(2-imidazolin-2-yl)-aminopyrimidine is obtained, (Melting point 267° C.) after recrystallization from nitromethane.

EXAMPLE 6

4-methoxy-2-methyl-6-methylthio-5-(2-imidazolin-2-yl)-aminopyrimidine 3.0 g 4-chloro-6-methoxy-2-methyl-5-(2-imidazolin-2-yl)-aminopyrimidine in 20 ml absolute toluene are mixed with a suspension of 1.2 g sodium-methyl mercaptide in 10 ml toluene and heated for 2 hours under stirring to 70° C. The processing is similar to Example 2. 1.2 g of 4-methoxy-2-methyl-6-methylthio-5-(2-imidazolin-2-yl)-aminopyrimidine is obtained. Melting point: 267° C.

The compunds 7–15 of the general formula (I) were prepared as described in the preceding examples, and are compiled in the following table.

| Example | $R^1$ | $R^2$ | $R^3$ | $R^4$ | Melting Point °C. | Salt | Preparation According to Example |
|---|---|---|---|---|---|---|---|
| 7 | Cl | Cl | H | Ac | 221 | — | 1 |
| 8 | $SCH_3$ | $SCH_3$ | H | H | 253 | — | 4 |
| 9 | Cl | $CH_3$ | Cl | Ac | 252 | — | 1 |
| 10 | $SCH_3$ | $CH_3$ | Cl | H | 230 | HCl | 2 |
| 11 | $SCH_3$ | $CH_3$ | $SCH_3$ | H | 200 | HCl | 4 |
| 12 | Cl | Cl | $C_2H_5$ | Ac | 211 | — | 1 |
| 13 | Cl | $OCH_3$ | $C_2H_5$ | H | 178 | HCl | 3 |
| 14 | $SCH_3$ | $OCH_3$ | $C_2H_5$ | H | 180 | — | 6 |
| 15 | $OCH_3$ | $SCH_3$ | Cyclopropyl | H | 248 (d) | — | +6 |

Ac = acetyl

EXAMPLE 16

2-cyclopropyl-4,6-dichloro-5-(1-acetyl-2-imidazolin-2-yl)-aminopyrimidine 7.0 g 5-amino-2-cyclopropyl-4,6-dichloropyrimidine, 4.9 g 1-acetyl-2-imidazolidin-2-one and 70 ml phosphorous oxide trichloride are heated for one hour under reflux. The excess phosphorous oxide trichloride is distilled off under vacuum and the residue is placed in ice water. After neutralization with potassium carbonate and extraction with chloroform, the organic phase is dried and concentrated. The residue is recrystallized from nitromethane. 6.5 g of 2-cyclopropyl-4,6-dichloro-5-(1-acetyl-2-imidazolin-2-yl)-amino-pyrimidine is obtained. Melting point 247° C. (decomp.).

EXAMPLE 17

4-chloro-2-cyclopropyl-6-methoxy-5-(2-imidazolin-2-yl)-aminopyrimidine 3.0 g 2-cyclopropyl-4,6-dichloro-5-(1-acetyl-2-imidazolin-2-yl)-aminopyrimidine are mixed with a solution of 0.5 g sodium methylate in 30 ml methanol and stirred for three hours at room temperature. Then about 20 ml of methanol is distilled off. After adding water and extracting with chloroform, the organic phase is dried and concentrated. 1.9 g of 4-chloro-2-cyclopropyl-6-methoxy-5-(2-imidazolin-2-yl)-aminopyrimidine is obtained; melting point 214° C. The hydrochloride obtained in known manner has a melting point of 200° C.

EXAMPLE 18

2-cyclopropyl-4,6-dimethoxy-5-(2-imidazolin-2-yl)-aminopyrimidine 3.0 g 2-cyclopropyl-4,6-dichloro-5-(1-acetyl-2-imidazolin-2-yl)-aminopyrimidine are mixed with a solution of 1.4 g sodium methylate in 15 ml methanol and heated for 6 hours under reflux. The solution then is concentrated, mixed with water, and extracted with chloroform. The chlorform phase is dried and concentrated. 1.8 g of 2-cyclopropyl-4,6-dimethoxy-5(2-imidazolin-2-yl)-aminopyrimidine (melting point 193°-195° C.) is obtained. The hydrochloride of this compound melts at 214°-216° C.

EXAMPLE 19

2-cyclopropyl-4,6-di-methylthio-5-(2-imidazolin-2-yl)-aminopyrimidine.

2.0 g 2-cyclopropyl-4,6-dichloro-5-(1-acetyl-2-imidazolin-2-yl)-aminopyrimidine in 10 ml toluene are mixed with a suspension of 0.8 g sodium-methyl mercaptide in 10 ml toluene and stirred for one hour at room temperature. Then toluene is distilled off under vacuum, and the residue is mixed with water and extracted with chloroform. The chloroform phase is concentrated and the residue purified by column chromatography (developer: chloroform/methanol 40:5). 0.8 g of 2-cyclopropyl-4,6-di-methylthio-5-(2-imidazolin-2-yl)-aminopyrimidine are obtained, which is converted in known manner to the hydrochloride. Melting point 252° C. (decomp.).

EXAMPLE 20

2-cyclopropyl-4,6-dichloro-5-aminopyrimidine (a) cyclopropane carboximide ethyl ether 33.6 g (0.92 mole) HCl are introduced at 0°-10° C. for three hours into a solution of 61.7 g (0.92 mole) cyclopropane-carboxylic nitrile in 52.6 ml (0.92 mole) absolute ethanol. Subsequently, the reaction mixture is stirred for 3-4 hours at about 10° C. until the mixture crystallizes. After purification and drying, 133 g of the hydrochloride of cyclopropane carboximideethylether, melting point 115°-117° C. (decomp.) is obtained.

(b) Cyclopropane carboximide amide

To 9 g (0.52 mole) NH$_3$ in 100 ml absolute ethanol are added, at 10° C., 65 g (0.435 mole) cyclopropane carboximide ethyl ether hydrochloride. After adding an additional 100 ml absolute ethanol, the reaction mixture is heated to 35° C. and then stirred for half an hour. After concentration of the solution, the residue is dissolved in 500 ml isopropyl ether and stirred vigorously until a crystalline product is deposited. After the crystals have been vacuum dried and washed, 51.2 g of cyclopropanecarboximideamide hydrochloride is obtained. Melting point 124°-126° C.

(c) 2-cyclopropyl-4,6-dihydroxy-pyrimidine

To a solution of 29.3 g sodium in 600 ml ethanol are added 63.5 ml (0.425 mole) malonic ester and 51 6 (0.425 mole) cyclopropanecarboximideamide hydrochloride and the mixture is heated for three hours under reflux. After concentration of the reaction mixture, the residue is dissolved in water and acidified with concentrated hydrochloric acid. The deposit obtained after cooling is vacuum dried, washed with water, alcohol and isopropyl ether, and dried. 57 g of 2-cyclopropyl-4,6-dihydroxy-pyrimidine is obtained. Melting point over 290° C.

(d) 2-cyclopropyl-4,6-dihydroxy-5-nitro-pyrimidine

To 128.8 ml acetic acid are added 50.57 ml fuming nitric acid without exceeding 20° C. 57 g (0.375 mole) 2-cyclopropyl-4,6-dihydroxy-pyrimidine are added in portions without exceeding a temperature of 15° C. Then the reaction mixture is stirred for half an hour at 15° C., mixed with ice, and the deposit is washed with lots of water and dried. 69.8 of 2-cyclopropyl-4,6-dihydroxy-5-nitro-pyrimidine is obtained. Melting point 230°-235° C. (decomp.).

(e) 2-Cyclopropyl-4,6-dicholoro-5-nitro-pyrimidine

To a suspension of 69.8 g (0.339 mole)-2-cyclopropyl-4,6-dihydroxy-5-nitro-pyrimidine in 280 ml POCl$_3$, are added in drops at 30° C., 70 ml N,N-diethylaniline. Then the mixture is heated for 3 hours to 60° C. and left standing overnight. Subsequently, the POCl$_3$ is distilled off, the residue cooled, mixed with 500 g of ice, stirred vigorously, vacuum dried, and washed with lots of water. After recrystallization from cyclohexane, 70.5 g of 2-cyclopropyl-4,6-dichloro-5-nitro-pyrimidine is obtained.

Melting point: 50°-52° C.

(f) 2-cyclopropyl-4,6-dichloro-5-amino-pyrimidine 70 g of 2-cyclopropyl-4,6-dichloro-5-nitropyrimidine are hydrated in the presence of 8.2 g Raney nickel in 700 ml ethanol at 100 bar for 6 hours at room temperature. The reaction product is first extracted with methylenechloride, then the solution is concentrated, and the residue dissolved in cyclohexane and recrystallized. 41 g of 2-cyclopropyl-4,6-dichloro-5-amino-pyrimidine is obtained.

Melting point 54° C.

EXAMPLE 21

4,6-dimethoxy-5-(2-imidazolin-2-yl)-aminopyrimidine

To a solution of 12.9 g ammonium thiocyanate in 120 ml absolute acetone are added slowly, in drops, 25.3 g benzoyl chloride. The solution is heated for 5 minutes under reflux, and then 27 g 5-amino-4,6-dimethoxy pyrimidine dissolved in 50 ml acetone, are added dropwise. The heating is continued for 1 hour more under reflux, then the mixture is cooled and put into 1.5 l water. Subsequently it is extracted with chloroform and dried over magnesium sulfate, the chloroform is distilled off, the residue mixed with ether and vacuum dried. Yield: 34 g (61%) N-benzoyl-N'-(4,6-dimethoxy-5-pyrimidyl)-thiourea, melting point 193° C.

34 g of the N-benzoyl thiourea are boiled in 30 ml 10% NaOH for 5 minutes. After cooling, the solution is acidified with concentrated HCl and the pH-value is brought to 9 by means of a 15% aqueous $NH_3$ solution. The precipitated crystals are vacuum dried and washed with water. 16 g (70%) N-(4,6-dimethoxy-5-pyrimidyl)-thiourea, melting point 210° C., is obtained.

16 g of this thiourea derivative are suspended in 3 l acetone and mixed with 25.5 g methyl iodide. The mixture is heated for 1 hour under reflux. After cooling, the precipitated crystals are vacuum dried, washed with acetone, and dried. 20 g (75%) of N-(4,6-dimethoxy-5-pyrimidyl)-S-methylisothiouronium iodide, melting point 215° C., is obtained.

A solution of 10.7 g of the isothiouronium iodide obtained above in 50 ml methanol is added in drops to a boiling solution of 3.5 g ethylene diamine in 10 ml methanol. Then the reaction mixture is heated for 6 hours under reflux. After cooling, the crystals are deposited and vacuum dried. The residue is taken up in water, the pH value is adjusted to 12 with alkali, and the residue is extracted with chloroform. Then the organic phase is dried and concentrated. 3.1 g (46%) of 4,6-dimethoxy-5-(2-imidazolin-2-yl)-aminopyrimidine, melting point 230° C., is obtained.

EXAMPLE 22

4,6-diethoxy-5-(2-imidazolin-2-yl)-aminopyrimidine

Similar to Example 21, N-(4,6-diethoxy-5-pyrimidyl)-thiourea (melting point 212° C.) is obtained from 5-amino-4,6-diethoxy-pyrimidine over N-benzoyl-N'-(4,6-diethoxy-5-pyrimidyl)-thiourea (melting point 162° C.). It is methylated to N-(4,6-diethoxy-5-pyrimidyl)-S-methylisothiouronium iodide (melting point 153° C.) and yields, with ethylene diamine, 4,6-diethoxy-5-(2-imidazolin-2-yl)-amino pyrimidine, melting point 176°–177° C.

EXAMPLE 23

2,4-dimethoxy-5-(2-imidazolin-2-yl)-aminopyrimidine

Like Example 21, N-(2,4-dimethoxy-5-pyrimidyl)-thiourea (melting point 175° C.) is obtained from 5-amino-2,4-dimethoxy pyrimidine over N-benzoyl-N'-(2,4-dimethoxy-5-pyrimidyl)-thiourea (melting point 182° C.). Methylation yields N-(2,4-dimethoxy-5-pyrimidyl)-S-methyl-isothiouronium iodide (melting point 166° C.), which yields, with ethylene diamine, 2,4-dimethoxy-5-(2-imidazolin-2-yl)-aminopyrimidine, melting point 194°–195° C.

EXAMPLE 24

4,6-dichloro-2-methyl-5-(1-acetyl-2-imidazolin-2-yl)-aminopyrimidine 20 g 5-amino-4,6-dichloro-2-methyl pyrimidine, 15 g 1-acetyl-2-imidazolin-2-one and 200 mg phosphorous oxide trichloride are stirred for 48 hours at 50° C. The excess phosphorous oxide trichloride is distilled off in a vacuum. The residue is placed in ice water and neutralized with potassium carbonate. Subsequently, it is extracted with chloroform, the chloroform solution is concentrated, and the residue crystallized from 700 ml methanol-acetic ester (1:1). 16.5 g (52%) 4,6-dichloro-2-methyl-5-(1-acetyl-2-imidazolin-2-yl)-aminopyrimidine, melting point 257° C., is obtained.

EXAMPLE 25

4-chloro-6-methoxy-2-methyl-5-(2-imidazolin-2-yl)-aminopyrimidine 10.0 g 4,6-dichloro-2-methyl-5-(1-acetyl-2-imidazolin-2-yl)-aminopyrimidine are boiled in 400 ml methanol for 48 hours under reflux. The solution is concentrated, and the residue mixed with warm tetrahydrofuran. The crystals are recrystallized from isopropanol/ether. 6.4 g (80%) of 4-chloro-6-methoxy-2-methyl-5-(2-imidazolin-2-yl)-aminopyrimidine is obtained as the hydrochloride, melting point 189° C. Melting point of the base 217°–219° C. (decomposition). $^1$H-NMR spectrum is DMSO-$d_6$, delta values in ppm: 2.53 (s, $CH_3$), 3.65 (s, N-$CH_2$—$CH_2$-N), 3.98 (s, $OCH_3$), 8.66 (twice NH, deuterizable).

EXAMPLE 26

4-chloro-6-ethoxy-2-methyl-5-(2-imidazolin-2-yl)-aminopyrimidine 3.0 g 4,6-dichloro-2-methyl-5-(1-acetyl-2-imidazolin-2-yl)-aminopyrimidine are introduced at room temperature into a solution of 0.5 g sodium in 10 ml ethanol. Subsequently, the solution is heated for 30 minutes to 75° C., filtered, the filtrate is concentrated, the residue is placed in ice water, and the crystals are vacuum dried. After recrystallization from nitromethane, 1.2 g (45%) of 4-chloro-6-ethoxy-2-methyl-5-(2-imidazolin-2-yl)-aminopyrimidine, melting point 221° C., is obtained.

EXAMPLE 27

4,6-dichloro-5-(1-acetyl-2-imidazolin-2-yl)-aminopyrimidine 15.0 g 5-amino-4,6-dichloro-pyrimidine, 13.8 g 1-acetyl-2-imidazolin-2-one and 460 ml phosphorous oxide trichloride are stirred for 12 hours at 50° C. The excess phosphorous oxide trichloride is vacuum distilled off. The residue is placed in ice water and neutralized with potassium carbonate. Subsequently, it is extracted with chloroform, the chloroform solution is concentrated, and the residue crystallized from nitromethane. 4,6-dichloro-5-(1-acetyl-2-imidazolin-2-yl)-aminopyrimidine is obtained.

Melting point 221° C.

EXAMPLE 28

4,6-dichloro-5-(2-imidazolin-2-yl)-aminopyrimidine 4.0 g 4,6-dichloro-5-(1-acetyl-2-imidazolin-2-yl)-aminopyrimidine are kept in 80 ml 50% acetic acid for 2 days at 60° C. Then the solution is concentrated, the residue taken up in water and extracted with chloroform, whereby the starting material and the byproducts are separated. Subsequently, the aqueous phase is alkalized, and the reaction product is extracted with chloroform. After concentration, 1.4 g (41%) 4,6-dichloro-5-(2-imidazolin-2-yl)-aminopyrimidine, melting point 197°–198° C., is obtained.

EXAMPLE 29

4-chloro-6-methoxy-5-(2-imidazolin-2-yl)-aminopyrimidine 3.5 g 4,6-dichloro-5-(1-acetyl-2-imidazolin-2-yl)-aminopyrimidine are introduced into 30 ml 1% sodium methylate solution. After three hours, the precipitate is vacuum dried, washed with water, and recrystallized from nitromethane. 2.1 g of 4-chloro-6-methoxy-5-(2-imidazolin-2-yl)-aminopyrimidine (melting point 212° C.), is obtained.

Compounds 30 to 40 of the general formula I are set forth in the following table and are prepared in accordance with the foregoing examples as indicated.

| Example | $R^1$ | $R^2$ | $R^3$ | $R^4$ | Melting °C. | Prepared Acc. to Example |
|---|---|---|---|---|---|---|
| 30 | Cl | H | Cl | Ac | 192 | 24 |
| 31 | Cl | H | Cl | H | 222 | 25 |
| 32 | CH$_3$ | CH$_3$ | CH$_3$ | Ac | 195 | 24 |
| 33 | CH$_3$ | CH$_3$ | CH$_3$ | H | 237 | 29 |
| 34 | Cl | CH$_3$ | Cl | Ac | 252 | 24 |
| 35 | Cl | CH$_3$ | Cl | H | 240(decomp.) | 29 |
| 36 | OCH$_3$ | CH$_3$ | Cl | H | 225 | 27 |
| 37 | OCH$_3$ | CH$_3$ | OCH$_3$ | H | 220 | 27 |
| 38 | OCH$_3$ | OCH$_3$ | CH$_3$ | H | 241(decomp.) | 27 |
| 39 | CH$_3$ | OCH$_3$ | CH$_3$ | Ac | 180 | 24 |
| 40 | CH$_3$ | OCH$_3$ | CH$_3$ | H | 216 | 27 |

Ac = acetyl

In substantial number of embodiments of the present invention have been expressly disclosed. It is, therefore, to be broadly construed and not to be limited except by the character of the claims appended hereto.

What we claim is:

1. Substituted 5-(2-imidazolin-2-yl)-amino-pyrimidines of the general formula (I)

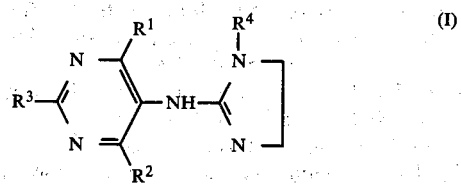

wherein $R^1$, $R^2$, and $R^3$ individually denote hydrogen or halogen, or alkoxy-, alkylthio- or alkyl group, each having 1 to 4 carbon atoms, or a cycloalkyl group with 3 to 5 carbon atoms, and $R^4$ represents hydrogen, formyl, acetyl, proprionyl, or butyryl, provided that $R^1$, $R^2$, $R^3$, and $R^4$ are not all hydrogen at the same time, and their physiologically compatible acid addition salts.

2. A pharmaceutical composition consisting essentially of an amount of at least one compound of claim 1 sufficient to lower blood pressure and a pharmaceutically acceptable additive.

3. A compound according to claim 1 wherein at least one of $R^1$ and $R^2$ is not hydrogen.

4. A compound according to claim 1 wherein at least one of $R^1$ and $R^2$ is halogen.

5. A compound according to claim 1 wherein $R^1$ is chlorine, $R^2$ is OCH$_3$, and $R^3$ is CH$_3$.

6. A compound according to claim 1 wherein $R^1$ is OCH$_3$, $R^2$ is CH$_3$ and $R^3$ is chlorine.

7. A compound according to claim 1 wherein $R^1$ and $R^3$ are CH$_3$ and $R^2$ is OCH$_3$.

8. A compound according to claim 1 wherein $R^1$ is chlorine, $R^2$ is OCH$_3$, and $R^3$ is n-propyl.

9. A compound according to claim 1 wherein $R^4$ is H.

* * * * *